United States Patent
Wada et al.

(10) Patent No.: US 10,312,291 B2
(45) Date of Patent: Jun. 4, 2019

(54) PHOTOELECTRIC CONVERSION DEVICE AND IMAGING DEVICE

(71) Applicant: Kabushiki Kaisha Toshiba, Minato-ku (JP)

(72) Inventors: Atsushi Wada, Kawasaki (JP); Isao Takasu, Setagaya (JP); Satomi Taguchi, Ota (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/267,889

(22) Filed: Sep. 16, 2016

(65) Prior Publication Data
US 2017/0110517 A1    Apr. 20, 2017

(30) Foreign Application Priority Data
Oct. 16, 2015 (JP) .................... 2015-204647

(51) Int. Cl.
*H01L 27/30* (2006.01)
*C07D 213/06* (2006.01)
(Continued)

(52) U.S. Cl.
CPC .......... *H01L 27/307* (2013.01); *C07D 213/06* (2013.01); *H01L 51/0059* (2013.01);
(Continued)

(58) Field of Classification Search
CPC ............ H01L 51/0072; H01L 51/0067; H01L 2251/308; H01L 27/307; H01L 51/0059; C07D 213/06
See application file for complete search history.

(56) References Cited

U.S. PATENT DOCUMENTS 6,483,099 B1 * 11/2002 Yu ..................... B82Y 10/00
250/214.1
2001/0010374 A1 * 8/2001 Takayama ........... H01L 27/3262
257/98
(Continued)

FOREIGN PATENT DOCUMENTS

EP    1672961 A1 * 5/2006 ........... C07D 213/06
JP    2008-63232 A * 3/2008 ........... C07D 213/06
(Continued)

OTHER PUBLICATIONS

Machine Translation of JP 2008-63232A (Kido et al) "Novel Heteroaryl-Based Compound Having Biphenyl Central Skeleton", Mar. 21, 2008, 34 pages.*
(Continued)

*Primary Examiner* — Caridad Everhart
(74) *Attorney, Agent, or Firm* — Oblon, McClelland, Maier & Neustadt, L.L.P.

(57) ABSTRACT

According to one embodiment, a photoelectric conversion device includes a first electrode, a second electrode, a photoelectric conversion layer provided between the first electrode and the second electrode, and a first layer provided
(Continued)

between the second electrode and the photoelectric conversion layer, the first layer including a phenyl pyridine derivative. The phenyl pyridine derivative is represented by formula (1) below,

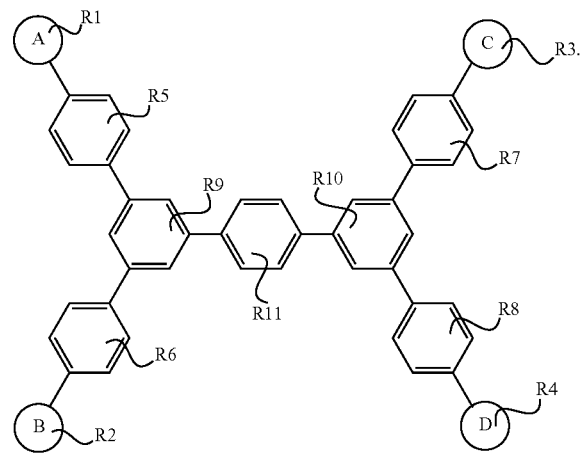

(1)

Rings A, B, C, and D in the formula (1) are pyridine rings. Each of R1 to R11 in the formula (1) is one selected from the group consisting of hydrogen, a straight-chain alkyl group, a branched alkyl group, an aryl group, and an electron-withdrawing heteroaryl group.

19 Claims, 4 Drawing Sheets

(51) Int. Cl.
| | | |
|---|---|---|
| *H01L 51/00* | (2006.01) | |
| *H01L 51/42* | (2006.01) | |
| *H01L 51/44* | (2006.01) | |
| *H01L 27/146* | (2006.01) | |

(52) U.S. Cl.
CPC ...... *H01L 51/0061* (2013.01); *H01L 51/0067* (2013.01); *H01L 51/4273* (2013.01); *H01L 51/442* (2013.01); *H01L 27/14665* (2013.01); *H01L 51/0072* (2013.01); *H01L 2251/308* (2013.01)

(56) References Cited

U.S. PATENT DOCUMENTS

| | | | | |
|---|---|---|---|---|
| 2003/0122749 | A1* | 7/2003 | Booth, Jr. | G09G 3/3208 345/82 |
| 2004/0251466 | A1* | 12/2004 | Nakamura | H01L 51/002 257/79 |
| 2006/0145145 | A1* | 7/2006 | Nishio | C07D 209/08 257/40 |
| 2009/0270589 | A1* | 10/2009 | Higuchi | C07D 213/53 528/423 |
| 2009/0289547 | A1* | 11/2009 | Ye | C07D 213/06 313/504 |
| 2010/0327265 | A1* | 12/2010 | Kimura | C07D 213/22 257/40 |
| 2011/0194000 | A1 | 8/2011 | Suzuki et al. | |
| 2011/0309344 | A1* | 12/2011 | Watanabe | H01L 51/0067 257/40 |
| 2012/0104941 | A1* | 5/2012 | Jung | C07D 239/26 313/504 |
| 2013/0270530 | A1 | 10/2013 | Watanabe et al. | |
| 2016/0301012 | A1* | 10/2016 | Han | H01L 51/0067 |
| 2016/0351828 | A1 | 12/2016 | Wada et al. | |

FOREIGN PATENT DOCUMENTS

| | | | |
|---|---|---|---|
| JP | 2011-187918 A | 9/2011 | |
| JP | 2012-80063 A | 4/2012 | |
| JP | 2015-214512 A | 12/2015 | |
| JP | 2016-222565 A | 12/2016 | |
| WO | WO2011115163 | * 9/2011 | ............ C07D 23/06 |

OTHER PUBLICATIONS

Kyoung Soo Yook, et al., "Thermally Stable Organic Solar Cells Using Small Molecule Exciton Blocking Layer" Electrochemical and Solid-State Letters, vol. 14, No. 6, 2011, pp. B59-B62.

* cited by examiner

PHOTOELECTRIC CONVERSION DEVICE AND IMAGING DEVICE

CROSS-REFERENCE TO RELATED APPLICATIONS

This application is based upon and claims the benefit of priority from Japanese Patent Application No. 2015-204647, filed on Oct. 16, 2015; the entire contents of which are incorporated herein by reference.

FIELD

Embodiments described herein relate generally to a photoelectric conversion device and an imaging device.

BACKGROUND

There are photoelectric conversion devices in which organic materials are used. Additionally, there are imaging devices in which photoelectric conversion devices are used. There is a need for improvements in thermal stability for photoelectric conversion devices.

DETAILED DESCRIPTION

According to one embodiment, a photoelectric conversion device includes a first electrode, a second electrode, a photoelectric conversion layer provided between the first electrode and the second electrode, and a first layer provided between the second electrode and the photoelectric conversion layer, the first layer including a phenyl pyridine derivative. The phenyl pyridine derivative is represented by formula (1) below, Rings A, B, C, and D in the formula (1) are pyridine rings. Each of R1 to R11 in the formula (1) is one selected from the group consisting of hydrogen, a straight-chain alkyl group, a branched alkyl group, an aryl group, and an electron-withdrawing heteroaryl group.

Various embodiments will be described hereinafter with reference to the accompanying drawings.

The drawings are schematic and conceptual; and the relationships between the thickness and width of portions, the proportions of sizes among portions, etc., are not necessarily the same as the actual values thereof. Further, the dimensions and proportions may be illustrated differently among drawings, even for identical portions.

In the specification and drawings, components similar to those described or illustrated in a drawing thereinabove are marked with like reference numerals, and a detailed description is omitted as appropriate.

First Embodiment

Figure 1:
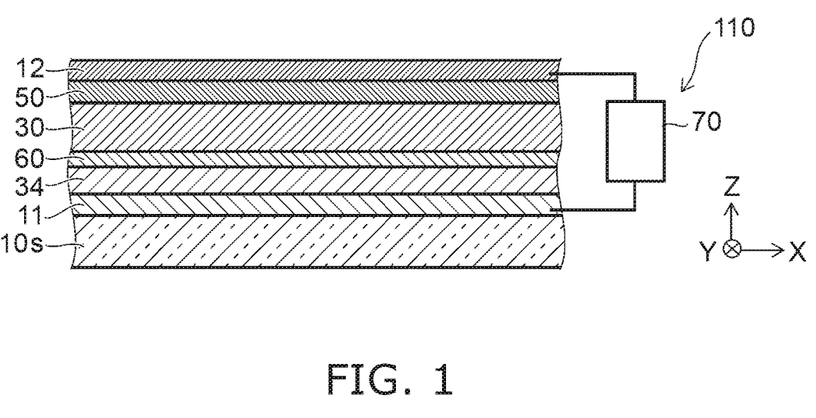
FIG. 1 is a schematic cross-sectional view illustrating a photoelectric conversion device according to a first embodiment.

FIG. 1 is a schematic cross-sectional view illustrating a photoelectric conversion device according to a first embodiment.

As shown in FIG. 1, the photoelectric conversion device 110 according to the embodiment includes a first electrode 11, a second electrode 12, a photoelectric conversion layer 30, and a first layer 50.

The second electrode 12 is separated along a first direction from the first electrode 11.

The first direction is defined as a "Z-axis direction". One direction perpendicular to the Z-axis direction is defined as an "X-axis direction". A direction perpendicular to both the Z-axis direction and the X-axis direction is defined as a "Y-axis direction".

The first electrode 11 and the second electrode 12 spread, for example, along an X-Y plane. The first electrode 11 and the second electrode 12 are substantially parallel to the X-Y plane.

The photoelectric conversion layer 30 is provided between the first electrode 11 and the second electrode 12. The first layer 50 is provided between the second electrode 12 and the photoelectric conversion layer 30.

In this example, a base body 10s is provided. The first electrode 11 is provided between the base body 10s and the second electrode 12. In this example, a second layer 60 is provided between the first electrode 11 and the photoelectric conversion layer 30. In this example, a flattening layer 34 is provided between the base body 10s and the second layer 60.

The photoelectric conversion layer 30 is disposed between the second layer 60 and the second electrode 12. The first layer 50 is disposed between the photoelectric conversion layer 30 and the second electrode 12.

The first layer 50 includes a phenyl pyridine derivative. This phenyl pyridine derivative is represented by formula (1) below.

(1)

In formula (1) above, rings A, B, C, and D are pyridine rings. In formula (1) above, each of R1 to R11 is one selected from the group consisting of hydrogen, a straight-chain alkyl group, a branched alkyl group, an aryl group, and an electron-withdrawing heteroaryl group.

One molecule of the compound represented by formula (1) above has seven benzene rings and the four pyridine rings A, B, C, and D. Each of the pyridine rings A, B, C, and D has a carbon atom at the position where each of the pyridine rings A, B, C, and D bonds with the benzene rings. Each of the pyridine rings A, B, C, and D bonds with the benzene rings at, for example, the third position. Each of the pyridine rings bonds with the benzene rings at, for example the fourth position. Each of the pyridine rings A, B, C, and D may bond with the benzene rings at mutually different positions.

The carbon atom included on the six-membered ring in each of the seven benzene rings may or may not include a substituent group. The carbon atom included on the six-membered ring in the four pyridine rings A, B, C, and D may or may not include a substituent group. For example, each of the R1 to R11 is one selected from the group consisting of hydrogen, a straight-chain alkyl group, a branched alkyl group, an aryl group, and an electron-withdrawing heteroaryl group. The number of carbon atoms included in each of the straight-chain alkyl group, the branched alkyl group, the aryl group, and the electron-withdrawing heteroaryl group is, for example, 6 or less.

In the electron-withdrawing group, the Hammett substituent constant is positive. In the embodiment, the electron-withdrawing heteroaryl group is, for example, a heteroaryl group that has a positive Hammett substituent constant.

In the embodiment, the R1 to R11 described above are, for example, identical to each other. In the embodiment, one of the R1 to R11 may be different from another one of the R1 to R11.

The first layer 50 includes the phenyl pyridine derivative described above and, as a result, high thermal stability, for example, is obtained. Thus, a photoelectric conversion device can be provided by which thermal stability can be improved. Examples of characteristics of the photoelectric conversion device 110 are described later.

The photoelectric conversion device 110 is, for example, an organic photoelectric conversion device. The photoelectric conversion device 110, for example, absorbs and photoconverts at least a portion of light that has entered the photoelectric conversion device 110.

Electrical characteristics between the first electrode 11 and the second electrode 12 vary depending on the incident light. For example, a controller 70 is provided. The controller 70 is electrically connected to the first electrode 11 and the second electrode 12. The controller 70 applies a potential difference between the first electrode 11 and the second electrode 12. For example, the controller 70 increases the potential of the second electrode 12 to be higher than the potential of the first electrode 11. The first electrode 11 becomes a cathode and the second electrode 12 becomes an anode. Due to this potential difference, current flowing between the first electrode 11 and the second electrode 12 varies depending on the intensity of the light that has entered the photoelectric conversion device 110. The photoelectric conversion device 110 may, for example, be used as an optical sensor.

The first electrode 11 includes, for example, a conductive, optically transparent material. The flattening layer 34 mitigates irregularities in, for example, the surface of the first electrode 11.

The second layer 60 suppresses, for example, the injection of electrons from the first electrode 11 toward the photoelectric conversion layer 30. The second layer 60 functions, for example, as an electron blocking layer. The second layer 60 transports holes generated at the photoelectric conversion layer 30 to the first electrode 11.

The light that has entered the photoelectric conversion device 110 enters the photoelectric conversion layer 30. The photoelectric conversion layer 30 absorbs and photoconverts at least a portion of this light, and generates electrons and holes.

The first layer 50 suppresses, for example, the injection of holes from the second electrode 12 toward the photoelectric conversion layer 30. The first layer 50 functions as, for example, a hole blocking layer. The first layer 50 transports electrons generated at the photoelectric conversion layer 30 to the second electrode 12.

The second electrode 12 is electrically connected to the photoelectric conversion layer 30. The second electrode 12 receives the electrons generated at the photoelectric conversion layer 30.

In this example, light that has entered the base body 10s enters the photoelectric conversion layer 30 via the first electrode 11, the flattening layer 34, and the second layer 60.

In the embodiment, the phenyl pyridine derivative included in the first layer 50 may, for example, include a compound represented by formula (2) below.

(2)

In the embodiment, the phenyl pyridine derivative included in the first layer 50 may, for example, include a compound represented by formula (3) below.

(3)

In the embodiment, the phenyl pyridine derivative included in the first layer 50 may, for example, include a compound represented by formula (4) below.

(4)

In the embodiment, the phenyl pyridine derivative included in the first layer 50 may, for example, include a compound represented by formula (5) below.

(5)

In formulas (2) to (5) above, the carbon atom included on the six-membered ring in each of the seven benzene rings may or may not include a substituent group. The carbon atom included on the six-membered ring in the four pyridine rings A, B, C, and D may or may not include a substituent group.

In formulas (2) to (4) above, for example, each of the R1 to R11 is one selected from the group consisting of hydrogen, a straight-chain alkyl group, a branched alkyl group, an aryl group, and an electron-withdrawing heteroaryl group (e.g. a heteroaryl group that has a positive Hammett substituent constant). The number of carbon atoms included in each of the straight-chain alkyl group, the branched alkyl group, the aryl group, and the electron-withdrawing heteroaryl group is, for example, 6 or less. The R1 to R11 may be identical to each other or may be different from each other.

Hereinafter, an example of the synthesis of the phenyl pyridine derivative included in the first layer 50 is described. In the following, an example of the synthesis of the compound represented by formula (3) above is described.

For example, 4-pyridine boronic acid pinacol ester, 1-bromo-3-iodobenzene, Pd(PPh$_3$)$_4$, and cesium carbonate are added to a dioxane solution and reacted. Thus, a first compound is obtained. Then, the first compound, bis(pinacolato)diboron, Pd(dppf)Cl$_2$, and potassium acetate are added to a DMAc solution and reacted. Thus, a second compound is obtained. The second compound, tribromobenzene, Pd(PPh$_3$)$_4$, and cesium carbonate are added to a dioxane solution and reacted. Thus, a third compound is obtained. The third compound, 1,4-phenylene diboronic acid, Pd(PPh$_3$)$_4$, and cesium carbonate are added to a dioxane solution and reacted. Thus, the compound represented by formula (3) is obtained. Purification is appropriately performed in the reactions described above.

A decomposition temperature of the compound represented by formula (3) above is, for example 532° C. Thus, the decomposition temperature of the compound represented by formula (3) is high. As a result of using the first layer 50 including the compound represented by formula (3), high thermal stability can be obtained.

In the following, an example of the synthesis of the compound represented by formula (5) above is described.

A first compound Com1 is obtained by the reaction represented by formula (6) below.

(6)

A second compound Com2 is obtained by the reaction represented by formula (7) below.

(7)

A third compound Com3 is obtained by the reaction represented by formula (8) below.

(8)

A fourth compound Com4 is obtained by the reaction represented by formula (9) below.

(9)

Com4

The fourth compound Com4 corresponds to the compound represented by formula (5) above. Purification is appropriately performed in the reactions of formula (6) to formula (9) above.

Hereinafter, examples of characteristics of the photoelectric conversion device 110 are described.

Figure 2:
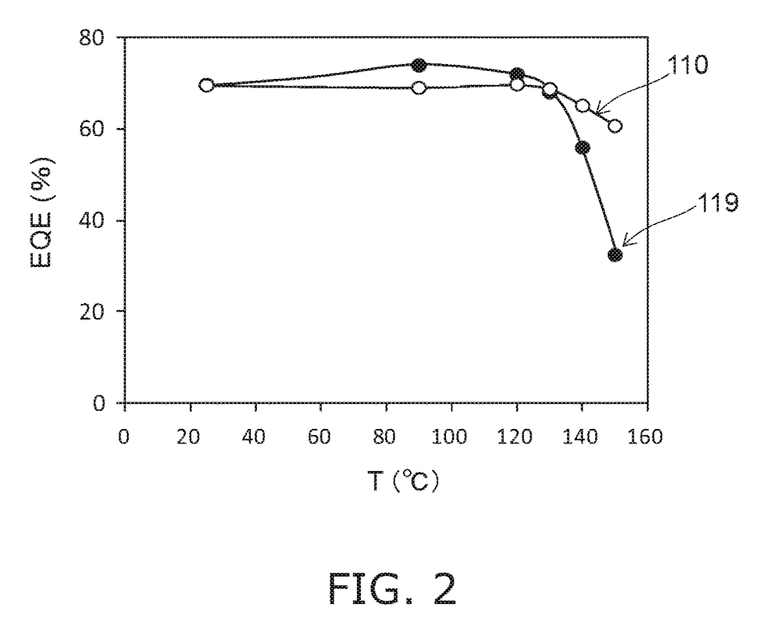
FIG. 2 is a graph illustrating characteristics of the photoelectric conversion device.

FIG. 2 is a graph illustrating characteristics of the photoelectric conversion device.

FIG. 2 shows external quantum efficiency (EQE) when the photoelectric conversion device 110 is annealed at various temperatures. The external quantum efficiency corresponds to photoelectric conversion efficiency. The annealing temperature T (° C.) is shown on the horizontal axis. The external quantum efficiency EQE (%) is shown on the vertical axis. The external quantum efficiency EQE is measured using a spectral response measurement device (CEP-V25ML, manufactured by Bunkokeiki Co., Ltd.). In the measurement, a wavelength of irradiation light is 530 nm. In the measurement, an output is 50 μW/cm².

In the photoelectric conversion device 110 of this example, the phenyl pyridine derivative included in the first layer 50 includes the compound represented by formula (3) above.

In FIG. 2, characteristics of a photoelectric conversion device 119 of a reference example are shown in the photoelectric conversion device 119, the compound represented by formula (10) below is used as the first layer 50.

(10)

In the photoelectric conversion devices 110 and 119, the following apply: the base body 10s is a glass substrate; the first electrode 11 is ITO; a thickness of the first electrode 11 is 50 nm; a thickness of the flattening layer 34 is 35 nm; a thickness of the second layer 60 is 3 nm; a thickness of the photoelectric conversion layer 30 is 80 nm; a thickness of the first layer 50 is 10 nm; the second electrode 12 is aluminum; and a thickness of the second electrode 12 is 150 nm.

In the photoelectric conversion devices 110 and 119, the external quantum efficiency EQE when the temperature T of the annealing is 25° C. is about 70%. In the photoelectric conversion device 119, when the temperature is 130° C. or higher, the external quantum efficiency EQE significantly declines. When the temperature T of the annealing is 150° C., the external quantum efficiency EQE is 61% in the photoelectric conversion device 110 and is 33% in the photoelectric conversion device 119. As a result of using the compound represented by formula (1) above as the first layer 50 (e.g. the hole blocking layer), high external quantum efficiency EQE can be obtained. As a result of using the compound represented by formula (1) as the first layer 50, high thermal stability can be obtained.

In the embodiment, for example, the first electrode 11 is a cathode and the second electrode 12 is an anode. Electrons are injected into the cathode. Holes are injected into the anode. The potential of the second electrode 12 is preferably higher than the potential of the first electrode 11; and current flows from the conductor with high potential to the conductor with low potential. As a result of using the compound represented by formula (1) as the first layer 50 (e.g. the hole blocking layer), for example, dark current, which is a cause of noise, is suppressed.

Further description of the example of the photoelectric conversion device 110 is given below.

The base body 10s, for example, supports the other members. A material that transmits light, for example, is used for the base body 10s. The base body 10s includes, for example, a glass substrate. The base body 10s includes, for example, a synthetic resin. The base body 10s is, for example, transparent. The base body 10s is, for example, optically transparent. The base body 10s transmits at least a portion of the light that enters the photoelectric conversion device 110.

For example, the base body 10s has strength sufficient to support the other members. The thickness, shape, structure, size, and the like of the base body 10s are not limited and may be selected in accordance with the use, purpose, and the like thereof.

The first electrode 11 is, for example, provided on the base body 10s. The first electrode 11 is, for example, in contact with the base body 10s. The first electrode 11 is electrically connected to the photoelectric conversion layer 30. The first electrode 12 receives the holes generated at the photoelectric conversion layer 30.

The first electrode 11 includes, for example, a conductive metal oxide film. The first electrode 11 may include, for example, a metal thin film. This metal thin film is, for example, optically transparent. The first electrode 11 may include an organic conductive polymer.

The metal oxide film included in the first electrode 11 includes, for example, at least one of indium oxide, zinc oxide, tin oxide, indium tin oxide (ITO), or fluorine-doped tin oxide (FTO). The first electrode 11 includes, for example, at least one oxide of indium, zinc, or tin. The oxide may include fluorine. The metal thin film included in the first electrode 11 includes, for example, at least one of gold, platinum, silver, or copper. The conductive polymer included in the first electrode 11 may, for example, include at least one of polyaniline or a derivative thereof. The conductive polymer may, for example, include at least one of polythiophene or a derivative thereof. The first electrode 11 preferably includes a transparent electrode of ITO. Hence, high light transmittance and high electrical conductivity can be obtained.

In cases where the first electrode 11 includes ITO, the thickness of the first electrode 11 is preferably not less than 30 and not more than 300 nm. At thicknesses of not less than 30 nm, the resistance of the first electrode 11 will decrease. Thus, declines in conversion efficiency due to increases in resistance can be suppressed. At thicknesses of not more than 300 nm, flexibility of the first electrode 11 can be maintained. Thus, cracking of the first electrode 11 can be suppressed.

The first electrode 11 is, for example, a single layer. The first electrode 11 may, for example, include a plurality of films. The plurality of films are stacked on each other. In this plurality of films, work functions may, for example, be different from each other.

The flattening layer 34 is, for example, in contact with the first electrode 11. The flattening layer 34 may, for example, include a mixture of poly(ethylene dioxythiophene) and poly(styrene sulfonic acid) (PEDOT:PSS). The flattening layer 34 may, for example, include a polythiophene polymer. The flattening layer 34 includes, for example, a conductive ink.

The second layer 60 includes, for example, at least one of N,N'-bis(3-methylphenyl)-N, N'-diphenylbenzidine (TPD), or tris(4-carbazoyl-9-yl-phenyl)amine (TCTA). In the embodiment, the material of the second layer 60 is not limited.

The photoelectric conversion layer 30 may, for example, include a donor material and an acceptor material. This donor material includes at least one of coumarin, quinacridone, or subphthalocyanine. This acceptor material includes, for example, at least one of fullerene (C60), perylene, or phthalocyanine.

The first layer 50 includes the compounds of formulas (1) to (5) above. A thickness of the first layer 50 is, for example, preferably not less than 3 and not more than 10 nm.

The second electrode 12 includes, for example, a conductive metal oxide film. For example, the second electrode 12 includes, for example, at least one oxide of indium, zinc, or tin. The second electrode 12 may include, for example, a conductive metal thin film. The second electrode 12 may, for example, include at least one of aluminum, silver, or gold. The second electrode 12 may include a compound. The compound includes at least one oxide including indium, zinc, or tin. The second electrode 12 may, for example, include an alloy. The alloy may include, for example, at least one of lithium-aluminum alloy, lithium-magnesium alloy, lithium-indium alloy, magnesium-silver alloy, magnesium-indium alloy, magnesium-aluminum alloy, indium-silver alloy, or calcium-aluminum alloy. The material of the second electrode 12 is not limited.

A thickness of the second electrode 12 is, for example, preferably not less than 10 and not more than 150 nm. At thicknesses of not less than 10 nm, low resistance, for example, can be obtained. At thicknesses of not more than 150 nm, time to form the second electrode 12 will be short. Thus, damage to the other layers at the time of film formation can be suppressed.

The second electrode 12 is, for example, a single layer. The second electrode 12 may include, for example, a plurality of films. The plurality of films are stacked on each other. In this plurality of films, work functions may, for example, be different from each other. Hereinafter, an example of a manufacturing method of the photoelectric conversion device 110 will be described.

A transparent conductive film of ITO or the like as the first electrode 11 is formed via a sputtering method on a glass substrate that becomes the base body 10s. At least one of a vacuum deposition method, a sputtering method, an ion plating method, a plating method, or a coating method is used, for example, in the forming of the first electrode 11.

A film of a conductive material of PEDOT:PSS or the like that becomes the flattening layer 34 is formed on the first electrode 11. The forming of the film is performed, for example, via a spin coating method or the like. Then, the film is subjected to drying by heating using a hot plate or the like. Thus, the flattening layer 34 is obtained. The solution to be coated may be filtered beforehand using a filter.

A film of, for example, TPD is formed as the second layer 60 on the flattening layer 34 via a vacuum deposition method. At least one of a vacuum deposition method or a coating method is used, for example, in the forming of the second layer 60.

A film of, for example, subphthalocyanine that becomes the photoelectric conversion layer 30 is formed on the second layer 60 via a vacuum deposition method. At least one of a vacuum deposition method or a coating method is used, for example, in the forming of the film that becomes the photoelectric conversion layer 30.

The first layer 50 is formed on the photoelectric conversion layer 30. At least one of a vacuum deposition method or a coating method is used, for example, in the forming of the first layer 50.

A film of, for example, aluminum that becomes the second electrode 12 is formed on the first layer 50 via a vacuum deposition method. At least one of a vacuum deposition method, a sputtering method, an ion plating method, a plating method, or a coating method is used in the forming of the second electrode 12. Hence, the photoelectric conversion device 110 is formed.

In the example shown in FIG. 1, the first electrode 11 is disposed between the base body 10s and the flattening layer 34. In the embodiment, the second electrode 12 is disposed between the base body 10s and the first layer 50.

In the embodiment, the base body 10s may be omitted. In the embodiment, the flattening layer 34 may be omitted. In the embodiment, the second layer 60 may be omitted.

In the embodiment, the material of the second electrode 12 may be the identical to or different from the material of the first electrode 11. For example, the first electrode 11 may include ITO and the second electrode 12 may include ITO.

For example, in the embodiment, the work function of the second electrode 12 is smaller than the work function of the first electrode 11. The second electrode 12 is, for example, aluminum.

The photoelectric conversion device 110 according to the embodiment is, for example, used in a sensor.

Examples of the sensor include organic stacked CMOS image sensors. The process of fabricating this sensor includes a heating process. Thermal stability of organic photoelectric conversion devices is insufficient and characteristics (e.g. conversion efficiency and the like) thereof are prone to degrading as a result of heating. Thus, improvements in the thermal stability of organic photoelectric conversion devices are desired.

In the embodiment, the compound represented by formula (1) above is used as the first layer 50. Thus, high thermal stability can be obtained in the photoelectric conversion device. Additionally, high thermal stability can be obtained in a solid-state imaging device.

Second Embodiment

The embodiment relates to an imaging device. The imaging device is, for example, a solid-state imaging device.

Figure 3:
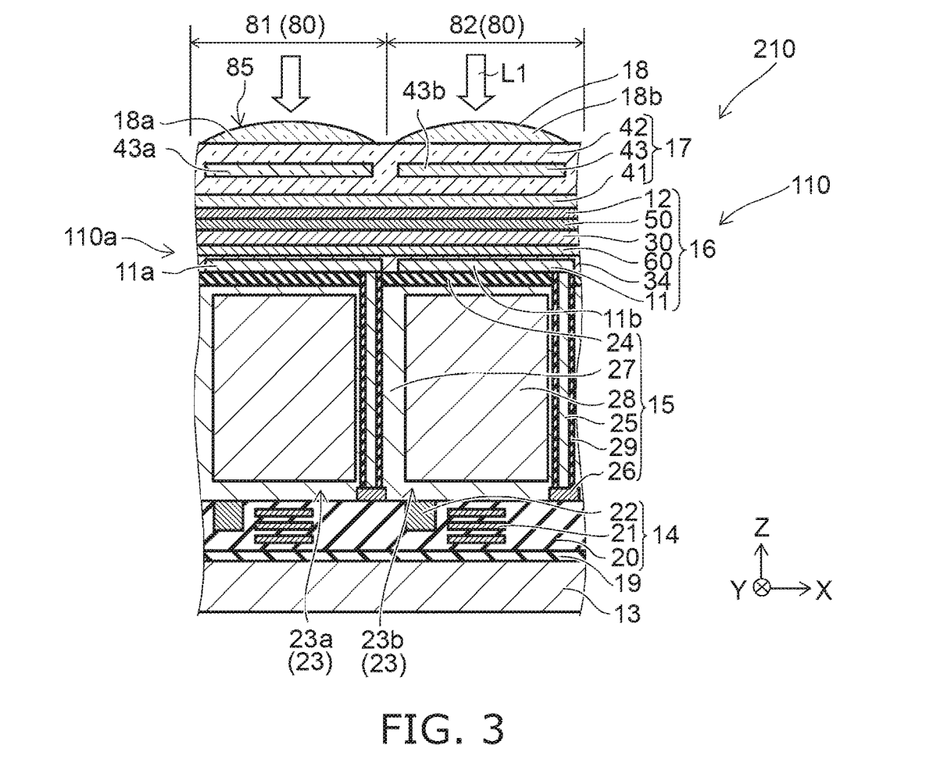
FIG. 3 is a schematic cross-sectional view illustrating an imaging device according to a second embodiment.

FIG. 3 is a schematic cross-sectional view illustrating an imaging device according to a second embodiment.

As shown in FIG. 3, an imaging device 210 includes a plurality of pixel regions 80. The plurality of pixel regions 80 includes, for example, a first pixel region 81 and a second pixel region 82. The second pixel region 82 is juxtaposed with the first pixel region 81 in a direction intersecting the Z-axis direction (in this example, the X-axis direction).

The number of the pixel regions 80 may, for example, be 4 or more. The plurality of pixel regions 80 may, for example, be juxtaposed along the X-axis direction and the Y-axis direction. The imaging device 210 includes a support substrate 13, an interconnect portion 14, a first photoelectric conversion portion 15, a second photoelectric conversion portion 16, a color filter portion 17, and a microlens portion 18.

The microlens portion 18 is separated in the Z-axis direction from the support substrate 13. The interconnect portion 14 is provided between the support substrate 13 and the microlens portion 18. The first photoelectric conversion portion 15 is provided between the interconnect portion 14 and the microlens portion 18. The second photoelectric conversion portion 16 is provided between the first photoelectric conversion portion 15 and the microlens portion 18. The color filter portion 17 is provided between the second photoelectric conversion portion 16 and the microlens portion 18.

In the imaging device 210, a surface where the microlens portion 18 is provided becomes a light receiving surface 85. Light L1 enters the light receiving surface 85.

The support substrate 13 supports the interconnect portion 14. A semiconductor substrate, for example, is used for the support substrate 13. A silicon (Si) substrate, for example, is used for the semiconductor substrate.

The interconnect portion 14 is provided on a light receiving surface 85 side of the support substrate 13. In this example, an adhesive layer 19 is provided between the interconnect portion 14 and the support substrate 13.

The interconnect portion 14 includes, for example, an insulating layer 20, a multilayer interconnection 21, and a read transistor 22.

The insulating layer 20 is provided between the adhesive layer 19 and the first photoelectric conversion portion 15. In this example, the insulating layer 20 is, for example, in contact with the adhesive layer 19 and the first photoelectric conversion portion 15. The insulating layer 20 includes, for example, silicon oxide ($SiO_2$).

The multilayer interconnection 21 is provided within the insulating layer 20. For example, a plurality of multilayer interconnections 21 are provided. One of the plurality of multilayer interconnections 21 is disposed in the first pixel region 81. Another of the plurality of multilayer interconnections 21 is disposed in the second pixel region 82.

A plurality of read transistors 22 are provided. One of the plurality of read transistors 22 is disposed in the first pixel region 81. Another of the plurality of read transistors 22 is disposed in the second pixel region 82.

The one of the plurality of multilayer interconnections 21 is electrically connected to the one of the plurality of read transistors 22. The another of the plurality of multilayer interconnections 21 is electrically connected to the another of the plurality of read transistors 22.

As described later, a plurality of storage diodes 26 are provided. The one of the plurality of multilayer interconnections 21 is electrically connected to one of the plurality of storage diodes 26. The another of the plurality of multilayer interconnections 21 is electrically connected to another of the plurality of storage diodes 26.

Each of the plurality of multilayer interconnections 21 is electrically connected to a peripheral circuit (not shown).

The multilayer interconnections 21 output electric charges stored in photodiodes 23 (described later) and the storage diodes 26 (described later) as signals to the peripheral circuits (not shown).

The multilayer interconnections 21 include, for example, at least one of copper (Cu), titanium (Ti), molybdenum (Mo), or tungsten (W). The multilayer interconnections 21 may, for example, include a high melting point metal. The multilayer interconnections 21 include, for example, at least one of titanium silicide (TiSi), molybdenum silicide (MoSi), or tungsten silicide (WSi). The multilayer interconnections 21 may, for example, include a silicide of a high melting point metal.

The read transistor 22 is provided on a surface of the interconnect portion 14 on the first photoelectric conversion portion 15 side. A plurality of read transistors 22 are provided. One of the plurality of read transistors 22 is provided in the first pixel region 81. Another of the plurality of read transistors 22 is provided in the second pixel region 82. The one of the plurality of read transistors 22 controls movement of the electric charge stored in one of the plurality of photodiodes 23, for example.

The first photoelectric conversion portion 15 is, for example, in contact with the interconnect portion 14 and the second photoelectric conversion portion 16. The first photoelectric conversion portion 15 includes a storage diode 26, a first conductivity type semiconductor region 27, a second conductivity type semiconductor region 28, an insulating film 29, a contact plug 25, and an optically transparent insulating layer 24.

For example, the first conductivity type is p-type and the second conductivity type is n-type. In this case, the first conductivity type semiconductor region 27 is, for example, a p-type single crystal Si substrate. The second conductivity type semiconductor region 28 is, for example, an n-type impurity diffusion region. In the embodiment, the first conductivity type may be n-type and the second conductivity type may be p-type.

A plurality of the photodiodes 23 are formed by the first conductivity type semiconductor region 27 and the second conductivity type semiconductor region 28. In this example, a plurality of second conductivity type semiconductor regions 28 are provided. A first photodiode 23a is formed by one of the plurality of second conductivity type semiconductor regions 28 and the first conductivity type semiconductor region 27. A second photodiode 23b is formed by another of the plurality of second conductivity type semiconductor regions 28 and the first conductivity type semiconductor region 27.

The plurality of photodiodes 23 are arranged in an array. The first photodiode 23a is provided in the first pixel region 81. The second photodiode 23b is provided in the second pixel region 82. Each of the plurality of photodiodes 23 absorbs and photoconverts light transmitted through the photoelectric conversion layer 30 (described later). The light that enters one of the plurality of photodiodes 23 is, for example, one of the three primary colors of light.

A P-N junction face is formed between the first conductivity type semiconductor region 27 and the second conductivity type semiconductor region 28.

The first conductivity type semiconductor region 27 is provided between the interconnect portion 14 and the optically transparent insulating layer 24. The first conductivity type semiconductor region 27 is, for example, in contact with the interconnect portion 14 and the optically transparent insulating layer 24. Si including p-type impurities is, for example, used for the first conductivity type semiconductor region 27. The p-type impurities include, for example, boron or the like. The p-type impurities are doped in the Si. The second conductivity type semiconductor region 28 is in contact with the first conductivity type semiconductor region 27. Si including n-type impurities is, for example, used for the second conductivity type semiconductor region 28. The n-type impurities include, for example, phosphorus or the like. The n-type impurities are, for example, ion implanted into the Si.

The optically transparent insulating layer 24 is provided between the first conductivity type semiconductor region 27 and the second photoelectric conversion portion 16. The optically transparent insulating layer 24 is, for example, in contact with the first conductivity type semiconductor region 27 and the second photoelectric conversion portion 16. The optically transparent insulating layer 24 transmits at least a portion of the light transmitted through the second photoelectric conversion portion 16 and causes that light to enter the first photoelectric conversion portion 15. The optically transparent insulating layer 24 electrically insulates the photoelectric conversion layer 30 (described later) from the first conductivity type semiconductor region 27. The optically transparent insulating layer 24 includes, for example, $SiO_2$ or the like.

The storage diodes 26 are provided between the interconnect portion 14 and the second photoelectric conversion portion 16. The contact plug 25 is provided between the storage diode 26 and the second photoelectric conversion portion 16. The insulating film 29 is provided between the contact plug 25 and the first conductivity type semiconductor region 27. The insulating film 29 includes, for example, a silicon nitride (SiN) film.

The contact plug 25 extends in the Z-axis direction within the first conductivity type semiconductor region 27. The contact plug 25 is electrically connected between the interconnect portion 14 and the second photoelectric conversion portion 16. A plurality of contact plugs 25 are provided. Each of the plurality of contact plugs 25 is provided corresponding to each of the plurality of pixel regions 80. One of the photodiodes 23 is provided between the plurality of contact plugs 25.

The contact plug 25 electrically connect the first electrode 11 (described later; e.g. a lower transparent electrode) and the storage diode 26. For example, the electric charge collected by the first electrode 11 (the lower transparent electrode) is moved to the storage diode 26 via the contact plug 25. The contact plugs 25 include, for example, Si or the like.

The storage diodes 26 temporarily store the electric charge collected by the first electrode 11 (the lower transparent electrode). A floating diffusion (not shown) is provided within the first conductivity type semiconductor region 27. The stored electric charge is sent to the floating diffusion from the storage diodes 26 and is converted to an electrical signal.

The second photoelectric conversion portion 16 is provided between the first photoelectric conversion portion 15 and the color filter portion 17. The second photoelectric conversion portion 16 is, for example, in contact with the first photoelectric conversion portion 15 and the color filter portion 17. The second photoelectric conversion portion 16 includes the first electrode 11 (e.g. the lower transparent electrode), the flattening layer 34, the second layer 60 (e.g. the electron blocking layer), the photoelectric conversion layer 30, the first layer 50 (e.g. the hole blocking layer), and the second electrode 12 (e.g. an upper transparent electrode).

The first electrode 11 (the lower transparent electrode) is provided on a surface on a side of the light receiving surface 85 of the optically transparent insulating layer 24. A plurality of first electrodes 11 are provided. Each of the plurality of first electrodes 11 is provided in each of the plurality of pixel regions 80. At least a portion of one of the first electrodes 11 overlaps one of the plurality of photodiodes 23 in the Z-axis direction. For example, the plurality of first electrodes 11 include a first electrode 11a and a first electrode 11b. The first electrode 11a overlaps the first photodiode 23a in the Z-axis direction. The first electrode 11b overlaps the second photodiode 23b in the Z-axis direction. The first electrode 11a is provided in the first pixel region 81. The first electrode 11b is provided in the second pixel region 82. The first electrode 11 (the lower transparent electrode) includes, for example, ITO or a similar optically transparent, conductive material.

The flattening layer 34 is provided between the first electrode 11 and the photoelectric conversion layer 30, and between the optically transparent insulating layer 24 and the photoelectric conversion layer 30. The flattening layer 34 is, for example, in contact with the first electrode 11, the photoelectric conversion layer 30, and the optically transparent insulating layer 24. The flattening layer 34 flattens, for example, irregularities in the surfaces of the first electrode 11 (the lower transparent electrode) and the optically transparent insulating layer 24.

The second electrode 12 (the upper transparent electrode) is provided on a surface on a side of the light receiving surface 85 of the photoelectric conversion layer 30. The second electrode 12 overlaps the plurality of photodiodes 23 in the Z-axis direction. In this example, the second electrode 12 is continuous in the plurality of pixel regions 80. The second electrode 12 (the upper transparent electrode) applies bias voltage supplied from outside to the photoelectric conversion layer 30.

As a result of the application of the bias voltage by the second electrode 12 (the upper transparent electrode), electric charges are generated in the photoelectric conversion layer 30, corresponding to the light that has entered the photoelectric conversion layer 30. The generated electric charges are collected in each of the plurality of first electrodes 11 (the lower transparent electrodes). The second electrode 12 (the upper transparent electrode) includes, for example, ITO or a similar optically transparent, conductive material.

The color filter portion 17 is provided between the second photoelectric conversion portion 16 and the microlens portion 18. The color filter portion 17 is, for example, in contact with the second photoelectric conversion portion 16 and the microlens portion 18. The color filter portion 17 includes a protective film 41, a flattening film 42, and a plurality of color filters 43. The plurality of color filters include, for example, a first color filter 43a and a second color filter 43b.

The protective film 41 is provided on a surface on a side of the light receiving surface 85 of the second electrode 12 (the upper transparent electrode). The protective film 41 is, for example, in contact with the second electrode 12. The protective film 41 is continuous in, for example, the first pixel region 81 and the second pixel region 82. The protective film 41 is, for example, insulative. The protective film 41 includes, for example, aluminum oxide ($Al_2O_3$).

The flattening film 42 is provided between the protective film 41 and the microlens portion 18. The flattening film 42 is, for example, in contact with the protective film 41 and the microlens portion 18. The flattening film 42 includes, for example, silicon dioxide or the like.

The first color filter 43a and the second color filter 43b are provided within the flattening film 42. At least a portion of the first color filter 43a overlaps the first electrode 11a and also overlaps the first photodiode 23a in the Z-axis direction. At least a portion of the second color filter 43b overlaps the first electrode 11b and also overlaps the second photodiode 23b in the Z-axis direction. The first color filter 43a absorbs light of a particular wavelength region and transmits light of other wavelength regions. The second color filter 43b absorbs light of a particular wavelength region and transmits light of other wavelength regions. The wavelength of light that the second color filter 43b absorbs differs from the wavelength of light that the first color filter 43a absorbs.

For example, the first color filter 43a absorbs blue light and transmits green light and red light. The second color filter 43b absorbs red light and transmits blue light and green light. In the embodiment, the wavelength of light that the second color filter 43b absorbs may, for example, be the same as the wavelength of light that the first color filter 43a absorbs.

By appropriately selecting the wavelength regions of light that the first color filter 43a and the second color filter 43b absorb, the wavelength region of the light that enters the photoelectric conversion layer 30 is selected.

The microlens portion 18 is provided on a side of the light receiving surface 85 of the color filter portion 17. A plurality of microlenses are provided. The microlens portion 18 includes a first microlens 18a, a second microlens 18b, and the like. The first microlens 18a overlaps, for example, the first photodiode 23a in the Z-axis direction. The second microlens 18b overlaps, for example, the second photodiode 23b in the Z-axis direction. A shape in the X-Y plane of one of the microlenses is, for example, substantially a circle. The light L1 that enters is condensed by the microlenses. An optical center of each of the plurality of microlenses is located, for example, at a center of each of the plurality of photodiodes 23. An area in the X-Y plane of one of the microlenses is, for example, larger than an area of the light receiving surface of one of the plurality of photodiodes 23.

In the imaging device 210, the compound of formula (1) above is used for the first layer 50. Thus, for example, an imaging device can be obtained for which thermal stability can be improved.

The imaging device 210 illustrated in FIG. 3 is, for example, a back-illuminated photoelectric conversion device. In the embodiment, the imaging device 210 may be a surface-illuminated photoelectric conversion device.

In the preceding, the "three primary colors of light" are the three colors of blue, green, and red. The wavelength region of the blue light (light of the blue wavelength region) is, for example, not less than 400 and not more than 500 nm. The wavelength region of the green light (light of the green wavelength region) is, for example, not less than 500 and not more than 600 nm. The wavelength region of the red light (light of the red wavelength region) is, for example, not less than than 600 and not more than 700 nm.

As described previously, the imaging device 210 includes any photoelectric conversion device (e.g. the photoelectric conversion device 110) according to the first embodiment, and the photoelectric conversion layer of variations thereof.

For example, a plurality of photoelectric conversion devices are provided. For example, a first photoelectric conversion device 110a, a second photoelectric conversion device 110b, and the like are provided. The first photoelectric conversion device 110a includes, for example, the first electrode 11a, a portion of the second electrode 12, a portion of the photoelectric conversion layer 30, and a portion of the first layer 50. The second photoelectric conversion device 110b includes, for example, the first electrode 11b, a portion of the second electrode 12, a portion of the photoelectric conversion layer 30, and a portion of the first layer 50.

The second electrode 12 of one of the plurality of photoelectric conversion devices (e.g. a first photoelectric conversion device 110a) is separated from the first electrode 11 (e.g. the first electrode 11a) of that one of the plurality of photoelectric conversion devices along a first direction (the Z-axis direction). At least a portion of the plurality of photoelectric conversion devices is juxtaposed along a second direction (e.g. the X-axis direction, the Y-axis direction, or the like) intersecting with the first direction. In the imaging device 210 according to the embodiments, the photodiodes 23 are further provided. As described previously, the second electrode 12 is separated along the first direction (the Z-axis direction) from the first electrode 11. The photodiodes 23 overlap the photoelectric conversion device 110 in the first direction. For example, the first photodiode 23a overlaps the first photoelectric conversion device 110a in the first direction. For example, the second photodiode 23b overlaps the second photoelectric conversion device 110b in the first direction.

Figure 4:
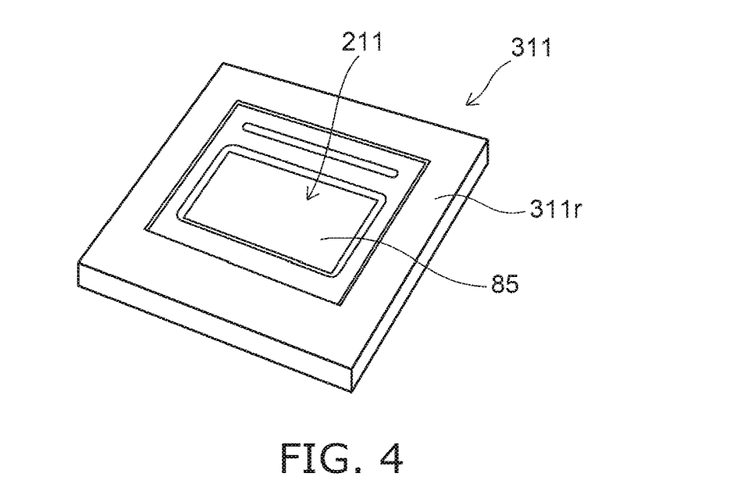
FIG. 4 is a perspective view illustrating a device that includes the imaging device according to the second embodiment.
Figure 5:
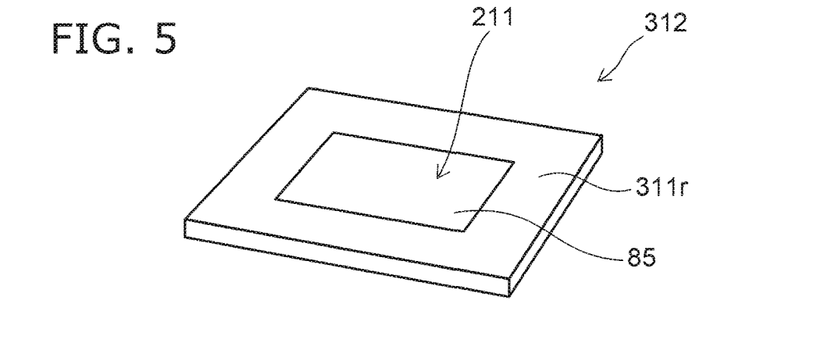
FIG. 5 is a perspective view illustrating another device that includes the imaging device according to the second embodiment.

FIG. 4 and FIG. 5 are perspective views illustrating devices that include the imaging device according to the second embodiment. FIG. 4 shows a CMOS image sensor 311. The CMOS image sensor 311 is, for example, a Full HD (1080p) type sensor. FIG. 5 shows a CMOS image sensor 312. The CMOS image sensor 312 is, for example, a VGA type sensor.

The CMOS image sensors 311 and 312 each include a solid-state imaging element 211 and a mold resin 311r. The solid-state imaging element 211 corresponds to the imaging device (and variations thereof) according to the embodiments.

The solid-state imaging element 211 includes a light receiving surface 85 and portions other than the light receiving surface 85. The mold resin 311r covers the portions other than the light receiving surface 85 of the solid-state imaging element 211. The solid-state imaging element 211 and the mold resin 311r are integrated. For example, the solid-state imaging element 211 is protected from external stress, moisture, contaminants, and the like.

The CMOS image sensors 311 and 312 are, for example, used for an imaging unit of a camera. The camera is, for example, a digital camera. The camera includes, for example, surveillance cameras, web cameras that use the internet, and the like. The camera may, for example, be mounted on a mobile terminal. The mobile terminal includes, for example, mobile phones. The mobile phones include, for example, smart phones (multifunction mobile phones). The mobile terminal also includes, for example, personal computers.

Figure 6:
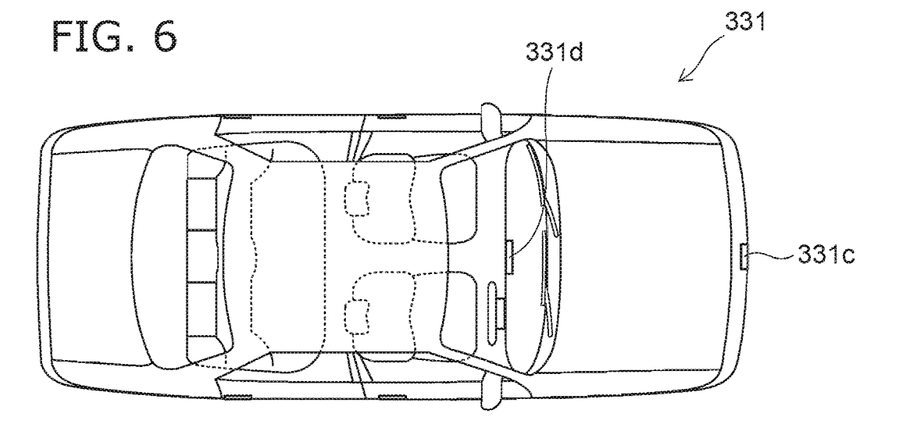
FIG. 6 is a plan view illustrating a moving body that includes the imaging device according to the second embodiment.
Figure 7:
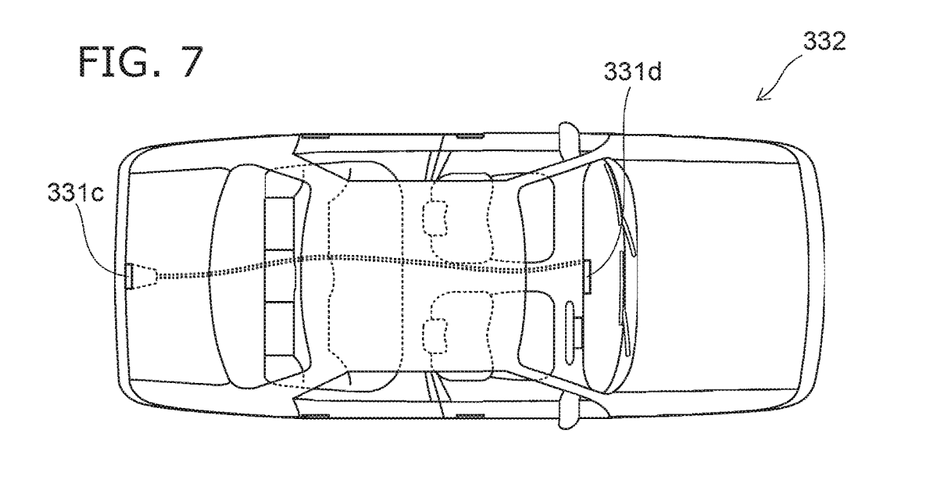
FIG. 7 is a plan view illustrating another moving body that includes the imaging device according to the second embodiment.

FIG. 6 and FIG. 7 are plan views illustrating moving bodies that include the imaging device according to the second embodiment.

FIG. 6 shows an example of a moving body 331 on which a camera 331c is mounted. The camera 331c is mounted, for example, at a front end portion of the moving body 331. The camera 331c captures images in front of the moving body 331. FIG. 7 shows an example of a moving body 332 on which a camera 331c is mounted. The camera 331c is mounted, for example, at a back end portion of the moving body 332. The camera 331c captures images behind the moving body 331.

For example, the CMOS image sensor 311 or the CMOS image sensor 312 described previously is used for the camera 331c.

The moving body 331 and the moving body 332 are, for example, vehicles. The moving body 331 and the moving body 332 may be airplanes, helicopters, boats, or the like.

Each of the moving body 331 and the moving body 332 further include a display 331d. The display 331d displays images captured by the camera 331c. The display 331d is, for example, provided in front of the driver's seat of each of the moving body 331 and the moving body 332.

In cases where the camera 331c is mounted at the front end portion of the moving body 331, a user checks images captured by the camera 331c on the display 331d. For example, when parking, there is a region that the user cannot directly see. In this example, the user can check this region using the display 331d.

In cases where the camera 331c is mounted at the back end portion of the moving body 332, a user checks images captured by the camera 331c on the display 331d. In this example, the user can check behind.

Figure 8:
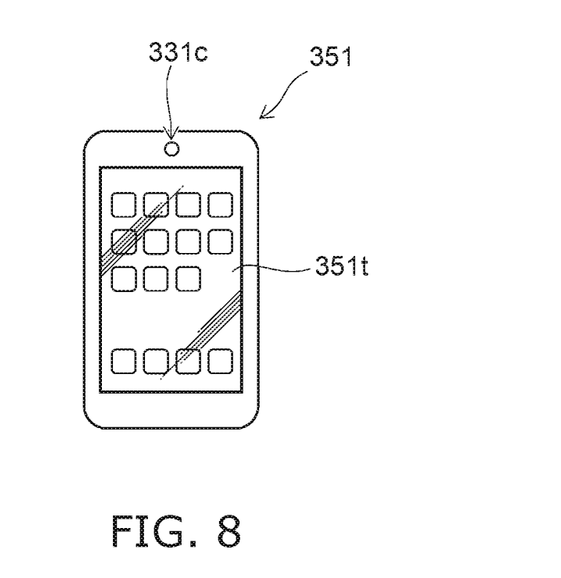
FIG. 8 is a plan view illustrating a device that includes the imaging device according to the second embodiment.
Figure 9:
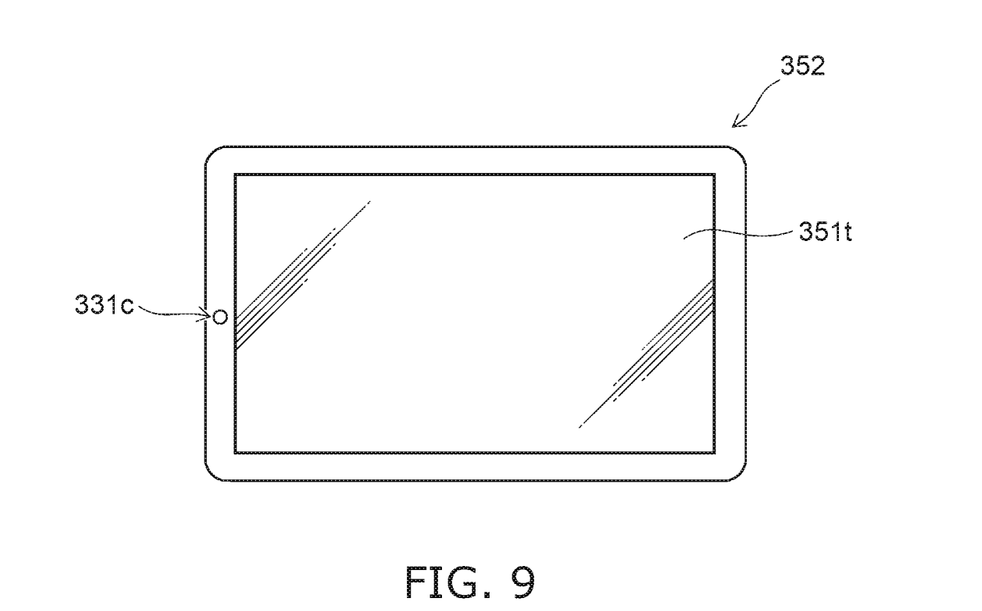
FIG. 9 is a plan view illustrating another device that includes the imaging device according to the second embodiment.

FIG. 8 and FIG. 9 are plan views illustrating devices that include the imaging device according to the second embodiment. FIG. 8 shows an example of an electronic device 351. The electronic device 351 is, for example, a smart phone (a multifunction mobile phone). FIG. 9 shows an example of another electronic device 352. The electronic device 352 is, for example, a tablet computer.

Each of the electronic device 351 and the electronic device 352 includes a camera 331c and a display panel 351t. The CMOS image sensor 311 or the CMOS image sensor 312 described previously is used for the camera 331c. The display panel 351t may have touch input functions. The display panel 351t may, for example, have touch panel functions.

The camera 331c is provided, for example, at an edge portion of a front face of the electronic device (the electronic device 351 or the electronic device 352). The camera 331c captures images on a front face side of the electronic device. The camera 331c may be provided, for example, on a back face of the electronic device (the electronic device 351 or the electronic device 352). The camera 331c may capture images on a back face side of the electronic device.

The display panel 351t is provided at, for example, the center of the front face of the electronic device. The display panel 351t displays images captured by the camera 331c.

According to the embodiments, a photoelectric conversion device capable of improving thermal stability and an imaging device can be provided.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in photoelectric conversion devices such as base bodies, electrodes, flattening layers, first layers, second layers, photoelectric conversion layers, and included in imaging devices such as interconnection portions, first photoelectric conversion portions, second photoelectric conversion portions, color filters, microlens portions, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all photoelectric conversion devices and imaging devices practicable by an appropriate design modification by one skilled in the art based on the photoelectric conversion devices and imaging devices described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A photoelectric conversion device comprising:
a first electrode;
a second electrode;

a photoelectric conversion layer provided between the first electrode and the second electrode; and a first layer provided between the second electrode and the photoelectric conversion layer, the first layer comprising a phenyl pyridine derivative represented by formula (1), wherein A, B, C, and D in the formula (1) are each a pyridine ring, and each of R1 to R11 in the formula (1) is independently hydrogen, a straight-chain alkyl group, a branched alkyl group, an aryl group, or an electron-withdrawing heteroaryl group.

2. The device according to claim 1, wherein the R1 to R11 are identical to each other.

3. The device according to claim 1, wherein one of the R1 to R11 is different from another one of the R1 to R11.

4. The device according to claim 1, wherein:

the phenyl pyridine derivative is represented by formula (2),

5. The device according to claim 1, wherein:

the phenyl pyridine derivative is represented by formula (3),

6. The device according to claim 1, wherein:

the phenyl pyridine derivative is represented by formula (4),

7. The device according to claim 1, wherein:
the phenyl pyridine derivative is represented by formula (5), (5)

8. The device according to claim 1, wherein a potential of the second electrode is higher than a potential of the first electrode.

9. The device according to claim 1, wherein a work function of the second electrode is smaller than a work function of the first electrode.

10. The device according to claim 1, wherein the first electrode comprises at least one oxide of indium, zinc, or tin.

11. The device according to claim 1, wherein
the second electrode comprises at least one of aluminum, silver, gold, lithium-aluminum alloy, lithium-magnesium alloy, lithium-indium alloy, magnesium-silver alloy, magnesium-indium alloy, magnesium-aluminum alloy, indium-silver alloy, calcium-aluminum alloy, or a compound which comprises an oxide of at least one of indium, zinc, or tin.

12. The device according to claim 1, wherein the photoelectric conversion layer comprises at least one of coumarin, quinacridone, subphthalocyanine, fullerene (C60), perylene, or phthalocyanine.

13. The device according to claim 1, wherein a thickness of the first layer is not less than 3 and not more than 10 nm.

14. The device according to claim 1, further comprising a controller electrically connected to the first electrode and the second electrode, and which increases the potential of the second electrode to be higher than the potential of the first electrode.

15. The device according to claim 1, further comprising a second layer provided between the first electrode and the photoelectric conversion layer.

16. The device according to claim 15, wherein the second layer comprises at least one of N,N'-bis(3-methylphenyl)-N,N'-diphenylbenzidine (TPD), or tris(4-carbazoyl-9-yl-phenyl)amine (TCTA).

17. An imaging device comprising a photoelectric conversion device,
the photoelectric conversion device comprising:
a first electrode;
a second electrode;
a photoelectric conversion layer provided between the first electrode and the second electrode; and
a first layer provided between the second electrode and the photoelectric conversion layer, the first layer comprising a phenyl pyridine derivative represented by formula (1), (1)

wherein A, B, C, and D in the formula (1) are each a pyridine ring, and
each of R1 to R11 in the formula (1) is independently hydrogen, a straight-chain alkyl group, a branched alkyl group, an aryl group, or an electron-withdrawing heteroaryl group.

18. The device according to claim 17, wherein,
a plurality of the photoelectric conversion device are provided,
the second electrode of one of the plurality of photoelectric conversion devices is separated along a first direction from the first electrode of the one of the plurality of photoelectric conversion devices, and
at least a portion of the plurality of photoelectric conversion devices is juxtaposed along a second direction intersecting with the first direction.

19. The device according to claim 17, further comprising:
a photodiode,
the second electrode being separated along a first direction from the first electrode, and
the photodiode overlapping the photoelectric conversion device in the first direction.

* * * * *